US010052077B2

(12) United States Patent
Jung et al.

(10) Patent No.: US 10,052,077 B2
(45) Date of Patent: Aug. 21, 2018

(54) TOMOGRAPHY IMAGING APPARATUS AND METHOD

(71) Applicant: SAMSUNG ELECTRONICS CO., LTD., Suwon-si (KR)

(72) Inventors: Jin-wook Jung, Seoul (KR); Toshihiro Rifu, Suwon-si (KR); Min-kook Cho, Hwaseong-si (KR); Eun-ji Seo, Seoul (KR); Kwan-hee Han, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 255 days.

(21) Appl. No.: 15/001,609

(22) Filed: Jan. 20, 2016

(65) Prior Publication Data
US 2016/0206269 A1 Jul. 21, 2016

(30) Foreign Application Priority Data
Jan. 20, 2015 (KR) .................. 10-2015-0009337

(51) Int. Cl.
*A61B 6/00* (2006.01)
*G06T 11/00* (2006.01)
*A61B 6/03* (2006.01)

(52) U.S. Cl.
CPC ............ *A61B 6/5258* (2013.01); *A61B 6/032* (2013.01); *A61B 6/4241* (2013.01); *A61B 6/482* (2013.01); *A61B 6/5205* (2013.01); *G06T 11/003* (2013.01)

(58) Field of Classification Search
CPC ....... A61B 6/032; A61B 6/4241; A61B 6/482; A61B 6/5205; A61B 6/5258; A61B 6/03; A61B 6/5211; A61B 6/582; A61B 6/583; G06T 11/003; G06T 11/005; G06T 2207/10081; G06T 7/0012
See application file for complete search history.

(56) References Cited

U.S. PATENT DOCUMENTS 9,149,241 B2 10/2015 Kim et al.
2006/0067461 A1* 3/2006 Yin ................. G06T 11/005
378/5
2006/0109949 A1 5/2006 Tkaczyk et al.
(Continued)

FOREIGN PATENT DOCUMENTS

JP 2013-192950 A 9/2013
KR 10-2013-0127356 A 11/2013
(Continued)

OTHER PUBLICATIONS

Machine translation of KR 101384511 published in 2014.*
(Continued)

*Primary Examiner* — Glen Kao
(74) *Attorney, Agent, or Firm* — Sughrue Mion, PLLC

(57) ABSTRACT

A tomography imaging apparatus and a tomography imaging method are provided. The tomography imaging apparatus includes a data acquirer configured to acquire first X-ray data of an object for each of energy bands, and an image preprocessor configured to perform a beam hardening correction on the first X-ray data for each of the energy bands, to generate second X-ray data of the object. The tomography imaging apparatus further includes an image reconstructor configured to reconstruct a tomography image of the object based on the second X-ray data.

15 Claims, 12 Drawing Sheets

(56) References Cited

U.S. PATENT DOCUMENTS

| | | | |
|---|---|---|---|
| 2011/0168878 A1* | 7/2011 | Hoerndler | G06T 11/005 |
| | | | 250/252.1 |
| 2011/0249879 A1 | 10/2011 | Wu et al. | |
| 2013/0182818 A1 | 7/2013 | Miyazaki | |
| 2013/0251097 A1 | 9/2013 | Zou | |
| 2013/0301799 A1 | 11/2013 | Kang et al. | |

FOREIGN PATENT DOCUMENTS

| | | |
|---|---|---|
| KR | 10-1384511 B1 | 4/2014 |
| KR | 10-1460616 B1 | 11/2014 |
| WO | 2012/029039 A1 | 3/2012 |

OTHER PUBLICATIONS

Flow Capture, "X-ray property", 3 pages total, http://www.flowcapture.com/technology_xray.html, 2013.
Communication issued Mar. 15, 2016, issued by the Korean Intellectual Property Office in counterpart Korean Patent Application No. 10-2015-0009337.
Search Report dated Apr. 25, 2016, issued by the International Searching Authority in counterpart International Patent Application No. PCT/KR2016/000549 (PCT/ISA/210).
Written Opinion dated Apr. 25, 2016, issued by the International Searching Authority in counterpart International Patent Application No. PCT/KR2016/000549 (PCT/ISA/237).
Communication issued by the European Patent Office dated Dec. 22, 2017 in counterpart European Patent Application No. 16740379.9.

\* cited by examiner

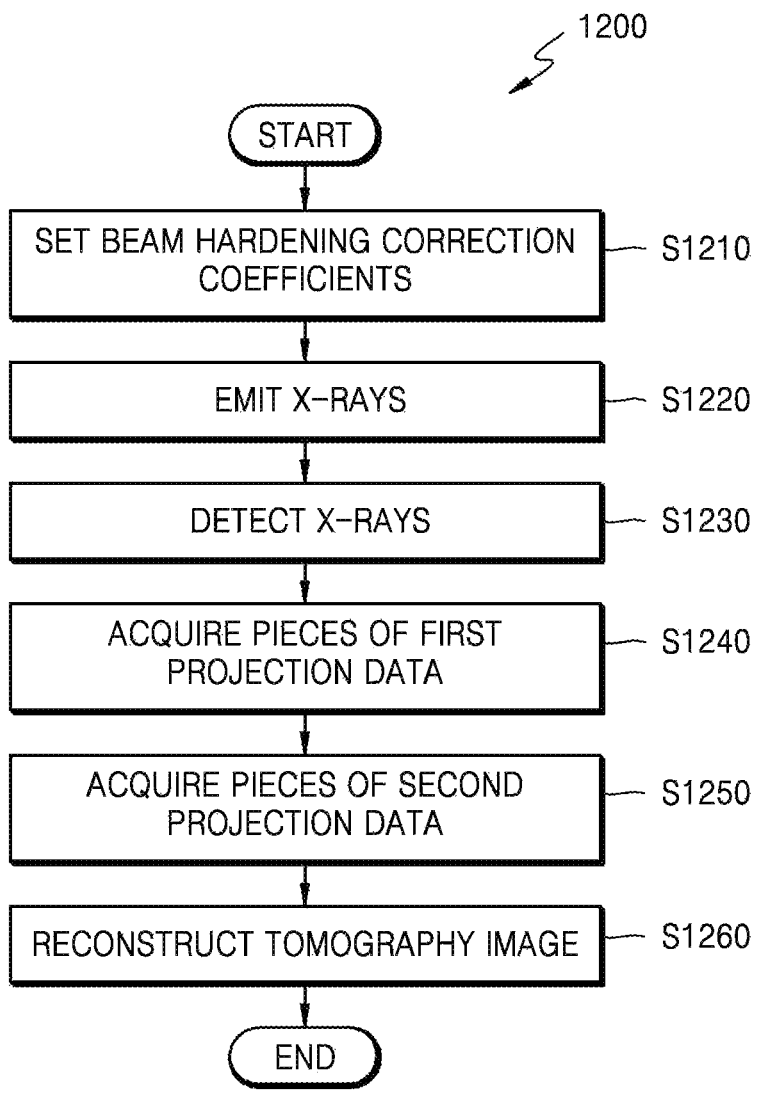

TOMOGRAPHY IMAGING APPARATUS AND METHOD

CROSS-REFERENCE TO RELATED APPLICATION

This application claims priority from Korean Patent Application No. 10-2015-0009337, filed on Jan. 20, 2015, in the Korean Intellectual Property Office, the disclosure of which is incorporated herein by reference in its entirety.

BACKGROUND

1. Field

Apparatus and methods consistent with exemplary embodiments relate to tomography imaging apparatuses and methods, and more particularly, to tomography imaging apparatuses and methods for correcting beam hardening.

2. Description of the Related Art

Medical imaging apparatuses are used to acquire images showing an internal structure of an object. The medical imaging apparatuses are non-invasive examination apparatuses that capture and process images of details of structures, tissue, fluid flow, etc., inside a body and provide the images to a user. A user, e.g., a medical practitioner, may use medical images output from the medical imaging apparatuses to diagnose a patient's condition and diseases.

A tomography imaging apparatus is used to obtain a tomography image of an object by emitting X-rays toward the object. Examples of the tomography imaging apparatus may include a computed tomography (CT) apparatus, a positron emission tomography (PET)-CT apparatus, and an optical coherence tomography (OCT) apparatus.

Among tomography imaging apparatuses, a CT apparatus is capable of providing a cross-sectional image of an object. Furthermore, the CT apparatus may represent an internal structure (e.g., organs such as a kidney, a lung, etc.) of the object without superimposing images, as compared to a general X-ray apparatus. Due to this, a CT apparatus has been widely used for precise diagnosis of diseases. A medical image acquired by a CT apparatus is hereinafter referred to as a CT image.

To obtain a CT image, a CT apparatus performs a CT scan of an object to acquire raw data. The acquired raw data is used to reconstruct a CT image. In this case, the raw data may be projection data obtained by projecting an X-ray onto the object or a projection data set called a sinogram.

For example, to obtain a CT image, image reconstruction may have to be performed using a sinogram obtained by performing a CT scan.

SUMMARY

Exemplary embodiments may address at least the above problems and/or disadvantages and other disadvantages not described above. Also, the exemplary embodiments are not required to overcome the disadvantages described above, and may not overcome any of the problems described above.

Tomography imaging apparatuses and methods for effectively correcting beam hardening are provided.

According to an aspect of an exemplary embodiment, there is provided a tomography imaging apparatus including a data acquirer configured to acquire first X-ray data of an object for each of energy bands, and an image preprocessor configured to perform a beam hardening correction on the first X-ray data for each of the energy bands, to generate second X-ray data of the object. The tomography imaging apparatus further includes an image reconstructor configured to reconstruct a tomography image of the object based on the second X-ray data.

The image preprocessor may be further configured to perform the beam hardening correction based on beam hardening correction coefficients corresponding to each of the energy bands.

The image preprocessor may be further configured to set the beam hardening correction coefficients based on at least one among an energy band, a tube voltage, and a number of slices to which the beam hardening correction coefficients correspond.

The image preprocessor may be further configured to determine the beam hardening correction coefficients corresponding to each of the energy bands, using a phantom.

The apparatus may further include an interface configured to receive an input for setting the energy bands.

The apparatus may further include an X-ray generator configured to emit X-rays toward the object.

The apparatus may further include a photon counting detector configured to detect X-rays for each of the energy bands.

According to an aspect of an exemplary embodiment, there is provided a tomography imaging method including acquiring first X-ray data of an object for each of energy bands, and performing a beam hardening correction on the first X-ray data for each of the energy bands, to generate second X-ray data of the object. The tomography imaging method further includes reconstructing a tomography image of the object based on the second X-ray data.

The performing may include performing the beam hardening correction based on beam hardening correction coefficients corresponding to each of the energy bands.

The method may further include setting the beam hardening correction coefficients based on at least one among an energy band, a tube voltage, and a number of slices to which the beam hardening correction coefficients correspond.

The method may further include determining the beam hardening correction coefficients corresponding to each of the energy bands, using a phantom.

The method may further include setting the beam hardening correction coefficients so that a gray value in the tomography image of a water phantom remains constant after the beam hardening correction.

The method may further include setting the beam hardening correction coefficients so that a rate of change in an attenuation amount of X-rays with respect to a penetration depth of the X-rays remains constant along the penetration depth.

The method may further include receiving an input for setting the energy bands.

The method may further include emitting X-rays toward the object.

The method may further include detecting X-rays for each of the energy bands, using a photon counting detector.

A non-transitory computer-readable storage medium may store a program to cause a computer to perform the method.

BRIEF DESCRIPTION OF THE DRAWINGS

The above and/or other aspects will be more apparent by describing exemplary embodiments with reference to the accompanying drawings, in which:

FIG. 12 is a flowchart of a tomography imaging method according to another exemplary embodiment.

DETAILED DESCRIPTION

Figure 1:
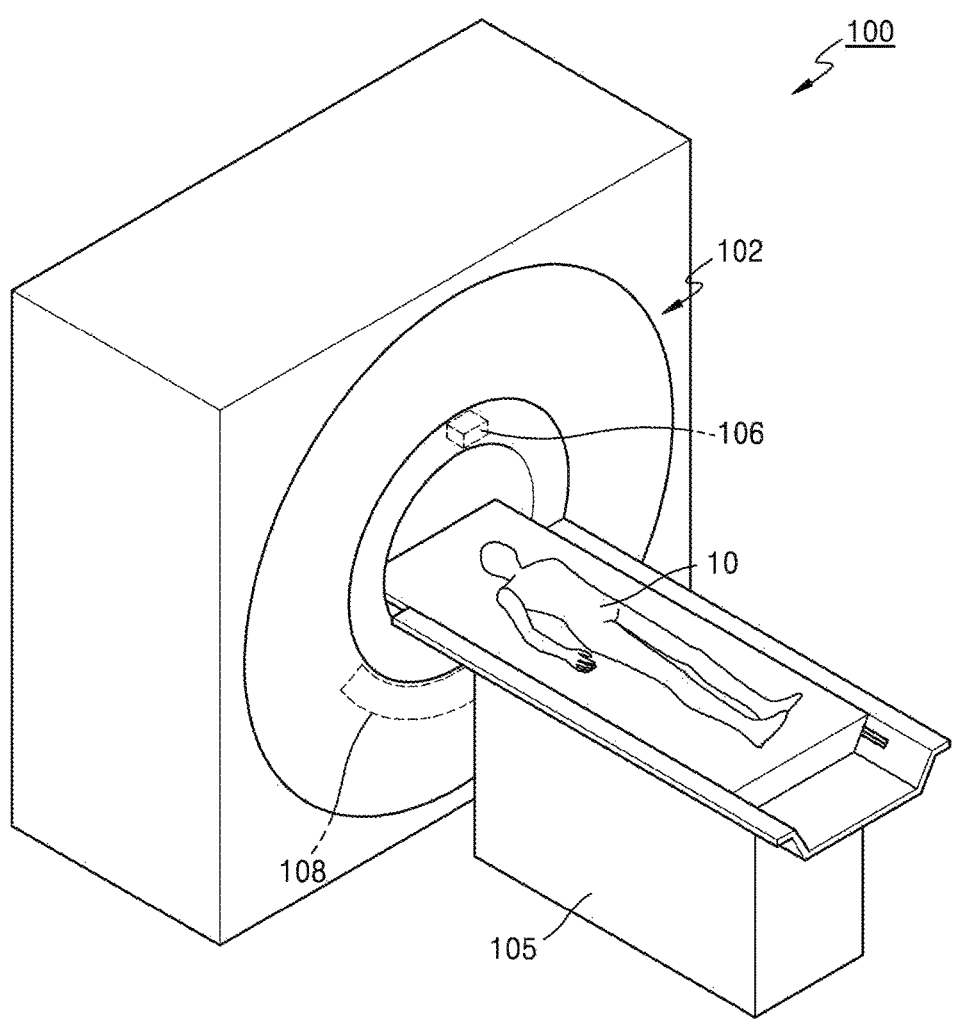
FIG. 1 is a schematic diagram of a computed tomography (CT) system according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

It will be understood that the terms "comprises" and/or "comprising" used herein specify the presence of stated features or components, but do not preclude the presence or addition of one or more other features or components. In addition, the terms such as "unit," "-er (-or)," and "module" described in the specification refer to an element for performing at least one function or operation, and may be implemented in hardware, software, or the combination of hardware and software.

Throughout the specification, an "image" may mean multi-dimensional data formed of discrete image elements, e.g., pixels in a two-dimensional (2D) image and voxels in a three-dimensional (3D) image. For example, the image may include a medical image of an object obtained by a computed tomography (CT) apparatus, a positron emission tomography-CT (PET-CT) apparatus, an optical coherence tomography (OCT) apparatus, or the like.

In the specification, a "tomography image" may be a composite image of a plurality of X-ray images obtained by scanning an object during rotation about at least one axis relative to the object. Examples of the tomography image may include a CT image, a PET-CT image, an OCT image, etc. Furthermore, the tomography image may include 2D and 3D tomography images, and may also be referred to as a cross-sectional image, a plane image, etc.

Throughout the specification, an "object" may be a human, an animal, or a portion of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medial image expert, or a technician who repairs a medical apparatus.

Because a tomography system is capable of providing a cross-sectional image of an object, the CT system may express an inner structure (e.g., an organ such as a kidney, a lung, etc.) of the object without an overlap therebetween, compared to a general X-ray capturing apparatus.

The tomography system may obtain a plurality of pieces of image data with a thickness not more than 2 mm for several tens to several hundreds of times per second and then may process the plurality of pieces of image data, so that the tomography system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels to allow a user to easily observe an area of interest in volume rendering.

Voxel of interest (VOI)—a method of displaying only a selected area in volume rendering.

A CT system 100 according to an exemplary embodiment will now be described with reference to FIGS. 1 and 2. The CT system 100 may include various types of devices.

FIG. 1 is a schematic diagram of the CT system 100 according to an exemplary embodiment. Referring to FIG. 1, the CT system 100 includes a gantry 102, a table 105, an X-ray generator 106, and an X-ray detector 108.

The gantry 102 includes the X-ray generator 106 and the X-ray detector 108.

An object 10 is positioned on the table 105.

The table 105 may move in a predetermined direction (e.g., at least one among up, down, right, and left directions)

during a CT imaging procedure. Also, the table 105 may tilt or rotate by a predetermined angle in a predetermined direction.

The gantry 102 may also tilt by a predetermined angle in a predetermined direction.

Figure 2:
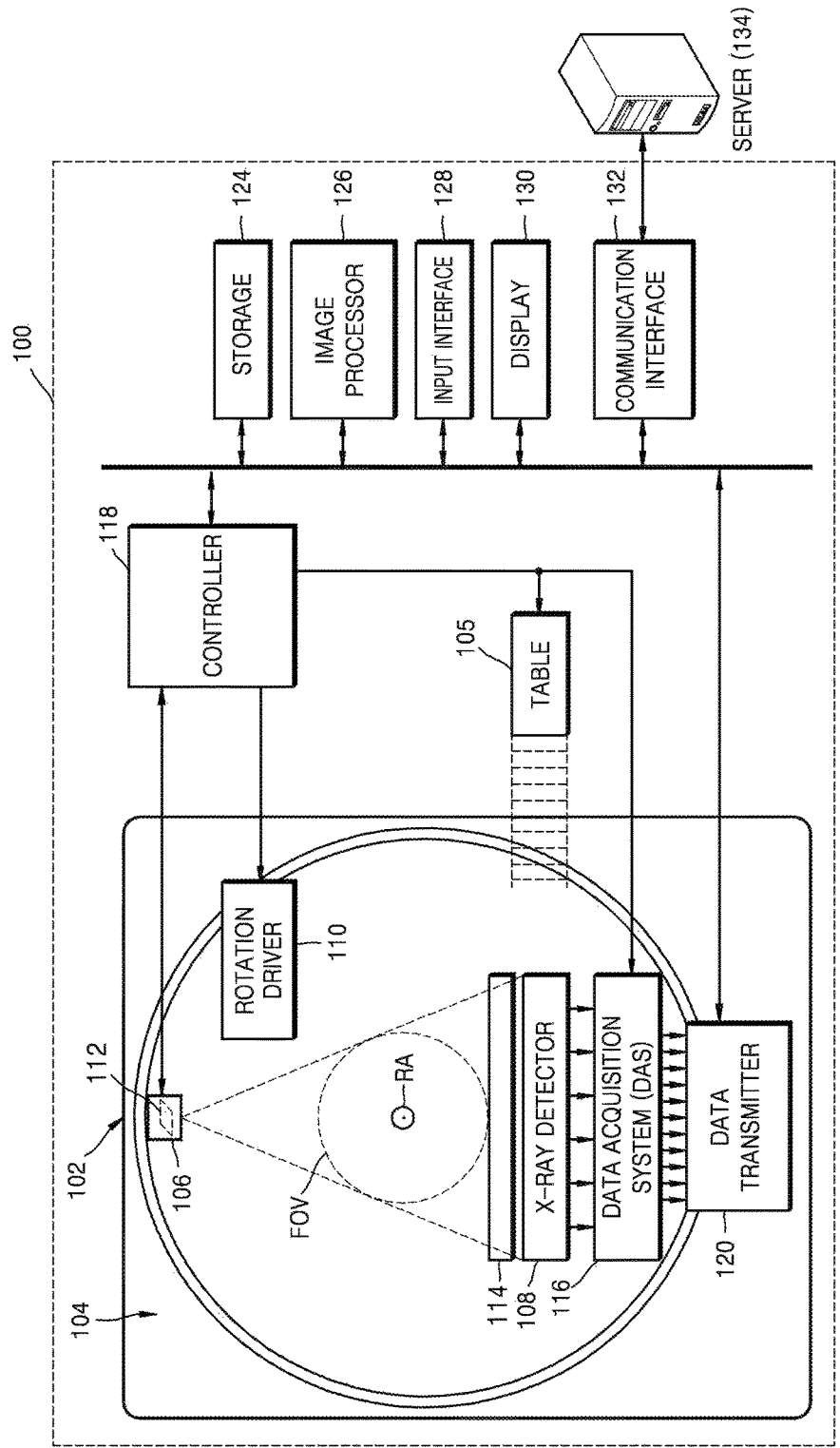
FIG. 2 is a block diagram of a structure of a CT system according to an exemplary embodiment.

FIG. 2 is a block diagram of a structure of the CT system 100 according to an exemplary embodiment.

The CT system 100 includes the gantry 102, the table 105, a controller 118, a storage 124, an image processor 126, an input interface 128, a display 130, and a communication interface 132.

As described above, the object 10 may be positioned on the table 105. In an exemplary embodiment, the table 105 may move in a predetermined direction (e.g., at least one among up, down, right, and left directions), and movement of the table 105 may be controlled by the controller 118.

The gantry 102 includes a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. Also, the rotating frame 104 may have a disc shape.

The rotating frame 104 includes the X-ray generator 106 and the X-ray detector 108 that are arranged to face each other to have predetermined field of view (FOV). The rotating frame 104 also includes an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. To transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring. Also, the rotating frame 104 may receive the driving signal and power from the rotation driver 110 via wireless communication.

The X-ray generator 106 may receive a voltage and current from a power distribution unit (PDU) via a slip ring and then a high voltage generator, and may generate and emit an X-ray. When the high voltage generator applies a predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 is emitted in a predetermined form due to a collimator 112.

The X-ray detector 108 may be positioned to face the X-ray generator 106. Each of a plurality of X-ray detecting devices may establish one channel, but one or more exemplary embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Also, the electrical signals generated by the X-ray detector 108 may be provided to an analog-to-digital converter via an amplifier.

According to a slice thickness or the number of slices, only some of a plurality of pieces of data collected by the X-ray detector 108 may be provided to the image processor 126 via the data transmitter 120, or the image processor 126 may select only some of the plurality of pieces of data.

Such a digital signal may be provided to the image processor 126 via the data transmitter 120. The digital signal may be provided to the image processor 126 by wire or wirelessly.

The controller 118 may control an operation of each of the elements in the CT system 100. For example, the controller 118 may control operations of the table 105, the rotation driver 110, the collimator 112, the DAS 116, the storage 124, the image processor 126, the input interface 128, the display 130, the communication interface 132, and the like.

The image processor 126 may receive data acquired by the DAS 116 (e.g., raw data that is data before processing), via the data transmitter 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data input to the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage 124 may include at least one storage medium among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processor 126 may reconstruct a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The input interface 128 may receive an external input with respect to an X-ray tomography imaging condition, an image processing condition, and the like. For example, the X-ray tomography imaging condition may include tube voltages, an energy value setting with respect to a plurality of X-rays, a selection of an imaging protocol, a selection of an image reconstruction method, a setting of an FOV area, the number of slices, a slice thickness, a parameter setting with respect to image post-processing, and the like. Also, the image processing condition may include a resolution of an image, an attenuation coefficient setting for the image, setting for an image combining ratio, and the like.

The input interface 128 may include a device for receiving a predetermined input from an external source. For example, the input interface 128 may include a microphone, a keyboard, a mouse, a joystick, a touch pad, a touch pen, a voice recognition device, a gesture recognition device, and the like.

The display 130 may display an X-ray image reconstructed by the image processor 126.

Exchanges of data, power, and the like between the aforementioned elements may be performed by using at least one among wired communication, wireless communication, and optical communication.

The communication interface 132 may perform communication with an external device, an external medical apparatus, etc. via a server 134 and the like. The communication will now be described with reference to FIG. 3.

Figure 3:
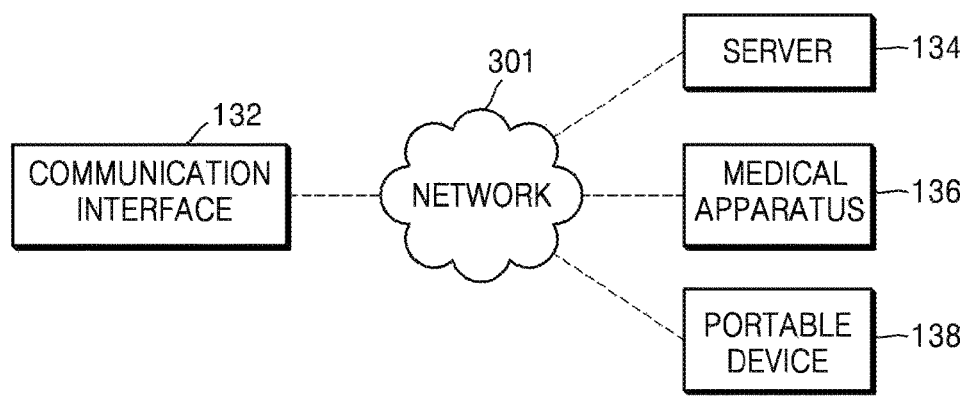
FIG. 3 is a block diagram of communication performed by a communication interface according to an exemplary embodiment.

FIG. 3 is a block diagram illustrating communication performed by the communication interface 132 according to an exemplary embodiment.

The communication interface 132 may be wire or wirelessly connected to a network 301 and therefore may perform communication with the server 134, a medical apparatus 136, and a portable device 138. The communication interface 132 may exchange data with a hospital server or other medical apparatuses in a hospital connected via a picture archiving and communication system (PACS).

Also, the communication interface 132 may perform data communication with the portable device 138 and the like, according to the digital imaging and communications in medicine (DICOM) standard.

The communication interface 132 may transmit and receive data related to diagnosing the object 10, via the network 301. Also, the communication interface 132 may transmit and receive a medical image obtained from the medical apparatus 136 such as a magnetic resonance imaging (MRI) apparatus, an X-ray apparatus, and the like.

Furthermore, the communication interface 132 may receive a diagnosis history or a medical treatment schedule about a patient from the server 134 and may use the diagnosis history or the medical treatment schedule to diagnose the patient. Also, the communication interface 132 may perform data communication not only with the server 134 or the medical apparatus 136 in a hospital but also with the portable device 138 of a user or patient.

Also, the communication interface 132 may transmit information about a device error, information about a quality control status, and the like to a system manager or a service manager via the network 301, and may receive feedback regarding the information from the system manager or service manager.

Beam hardening means a change in beam quality, i.e., results in an increase in an average energy of a beam (i.e., an X-ray) and thus a greater penetrating power thereof. Beam hardening induces various types of artifacts during reconstruction of a tomography image, which may hamper image-based diagnosis.

As described above, when a voltage (or tube voltage) is applied to an X-ray generator, the X-ray generator emits polychromatic radiation having a continuous energy spectrum. An attenuation coefficient of an object varies according to energy of an incident photon. In detail, an attenuation coefficient of an object is relatively high at a low photon energy, while an attenuation coefficient of the object is relatively low at a high photon energy. Thus, as a beam passes through the object, low energy photons are greatly attenuated, resulting in a decrease in the total energy of the beam but an increase in the average energy of the beam, which is called a beam hardening effect. Furthermore, due to the non-uniformity of an attenuation coefficient with respect to energies of photons, the magnitude of a beam hardening effect may vary according to energy bands.

Thus, in a tomography imaging apparatus and method according to exemplary embodiments, artifacts caused by beam hardening may be effectively removed and the quality of a tomography image may be improved by correcting the beam hardening by taking into account energy bands of photons.

Hereinafter, a tomography imaging apparatus and method according to exemplary embodiments will be described in detail with reference to the figures.

Figure 4:
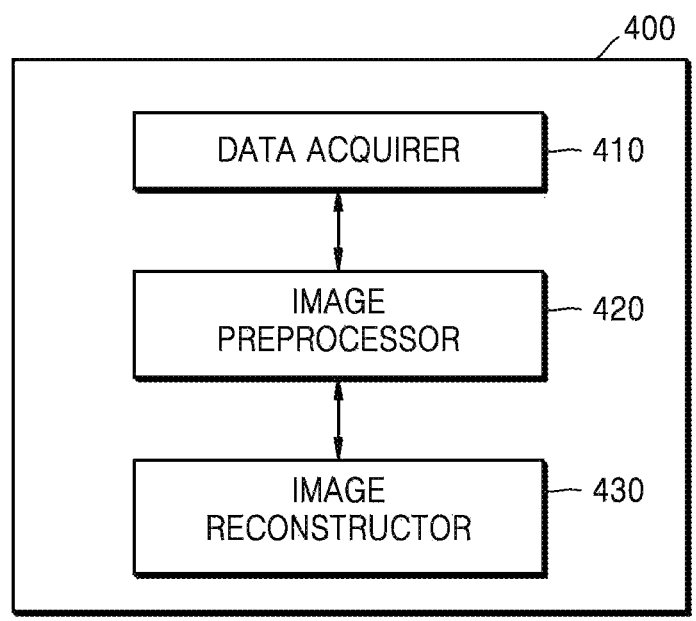
FIG. 4 is a block diagram of a structure of a tomography imaging apparatus according to an exemplary embodiment.

FIG. 4 is a block diagram of a structure of a tomography imaging apparatus 400 according to an exemplary embodiment.

Referring to FIG. 4, the tomography imaging apparatus 400 according to an exemplary embodiment includes a data acquirer 410, an image preprocessor 420, and an image reconstructor 430. However, all the components shown in FIG. 4 are not essential components. The tomography imaging apparatus 400 may include fewer or more components than those shown in FIG. 4.

Furthermore, the tomography imaging apparatus 400 may be included in the CT system 100 described with reference to FIGS. 1 and 2. In detail, the data acquirer 410, the image preprocessor 420, and the image reconstructor 430 may correspond to or be included in the image processor 126 of the CT system 100 of FIGS. 1 and 2. Thus, the same descriptions as those provided above with respect to FIGS. 1 and 2 are omitted.

Furthermore, the tomography imaging apparatus 400 may be included in the medical apparatus 136 or portable device 138 described with reference to FIG. 3, and be connected to the CT system 100 to operate.

The data acquirer 410 acquires pieces of first projection data for the object for each of a plurality of energy bands, from a photon counting detector that separately detect X-rays for each of the plurality of energy bands.

As described above with reference to FIGS. 1 and 2, an X-ray detector may be classified into a direct-type detector and an indirect-type detector according to a method of converting X-rays into an electrical signal. The direct-type detector directly detects electron-hole pairs created by emission of X-rays as an electrical signal. The indirect-type detector converts X-rays into light in a visible wavelength range using a scintillator and then detects the light as an electrical signal.

A general tomography imaging apparatus uses an integral detector that is an indirect-type detector that is not able to discriminate between energy bands of photons. Thus, in the general tomography imaging apparatus, a beam hardening correction process is performed for photons distributed over a wide range of energy spectrum without distinguishing between energies of the photons.

On the other hand, the tomography imaging apparatus 400 according to an exemplary embodiment use a photon counting detector that is configured to detect photons by distinguishing energies of the photons to correct beam hardening differently according to energy band.

If the tomography imaging apparatus 400 is included in the CT system 100 described with reference to FIGS. 1 and 2, the data acquirer 410 may acquire pieces of first projection data as the pieces of first projection data pass through a photon counting detector, the DAS 116, and the data transmitter 120.

The pieces of first projection data, i.e., unprocessed raw data, may be a set of data values corresponding to intensity of X-rays that have passed through the object.

The image preprocessor 420 acquires pieces of second projection data for the object by performing a beam hardening correction process on the pieces of the first projection data for each of the plurality of energy bands.

In detail, the image preprocessor 420 performs a beam hardening correction process by taking into account a variation of the magnitude of a beam hardening effect according to energy band. For example, the image preprocessor 420 may perform a beam hardening correction process on pieces of first projection data in a low energy band to a greater extent than on pieces of first projection data in a high energy band.

In addition to the beam hardening correction process, the image preprocessor 420 may correct non-uniformity of sensitivity to X-rays across channels, a drastic reduction in signal intensity, loss of a signal due to X-ray absorbing material such as metal, etc.

The image reconstructor 430 reconstructs a tomography image of the object based on the pieces of second projection data. The tomography image of the object includes 2D and 3D tomography images. In other words, the image reconstructor 430 may generate a 3D image of the object based on an acquired second projection data set, by using cone beam reconstruction algorithms, etc.

Beam hardening artifacts may be effectively removed from the tomography image of the object generated by the image reconstructor 430.

Figure 5:
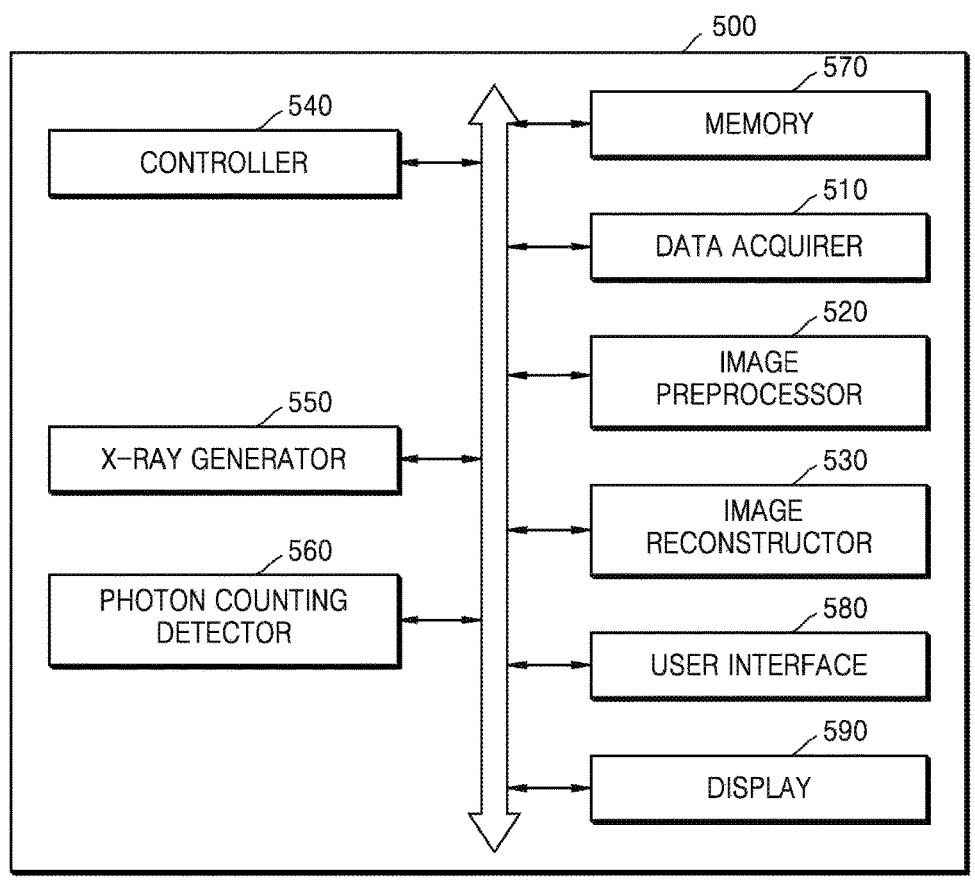
FIG. 5 is a block diagram of a structure of a tomography imaging apparatus according to another exemplary embodiment.

FIG. 5 is a block diagram of a structure of a tomography imaging apparatus 500 according to another exemplary embodiment.

Referring to FIG. 5, the tomography imaging apparatus 500 according to another exemplary embodiment includes a data acquirer 510, an image preprocessor 520, an image reconstructor 530, a controller 540, an X-ray generator 550, a photon counting detector 560, a memory 570, a user interface 580, and a display 590, in comparison to the tomography imaging apparatus 400 of FIG. 4. The components of the tomography imaging apparatus 500 of FIG. 5 may correspond to their counterparts in the tomography imaging apparatus 400 of FIG. 4. In detail, the data acquirer 510, the image preprocessor 520, and the image reconstructor 530 may respectively correspond to the data acquirer 410, the image preprocessor 420, and the image reconstructor 430. Thus, the same descriptions as those provided above with respect to FIG. 4 are omitted.

Furthermore, the tomography imaging apparatus 500 may be included in the CT system 100 described with reference to FIGS. 1 and 2. In detail, the data acquirer 510, the image preprocessor 520, and the image reconstructor 530 may be included in the image processor 126 of the CT system 100. Furthermore, the controller 540, the X-ray generator 550, the memory 570, the user interface 580, and the display 590 may correspond to or be included in the controller 118, the X-ray generator 106, the storage 124, the input interface 128, and the display 130, respectively. In addition, the photon counting detector 560 of the tomography imaging apparatus 500 may correspond to or be included in the X-ray detector 108 of the CT system 100, or may be included in the X-ray detector 108 and the DAS 116 of the CT system 100, depending on an exemplary embodiment. Thus, the same descriptions as those provided above with respect to FIGS. 1 and 2 are omitted.

The controller 540 may control an operation of each component in the tomography imaging apparatus 500. For example, the controller 540 may control the data acquirer 510, the image preprocessor 520, the image reconstructor 530, the X-ray generator 550, the photon counting detector 560, the memory 570, the user interface 580, the display 590, etc.

The X-ray generator 550 emits X-rays toward an object. In detail, the X-ray generator 550 may generate X-rays having a plurality of energy spectra that correspond to a tube voltage and emit the X-rays toward the object.

The photon counting detector 560 separately detects X-rays for each of the plurality of energy bands. In detail, the photon counting detector 560 may separately detect X-rays emitted by the X-ray generator 550 toward the object for each of the plurality of energy bands.

The photon counting detector 560 will be described in more detail below with reference to FIG. 10.

The memory 570 may store pieces of information and data for generating a tomography image, or pieces of information and data acquired during generation of the tomography image. For example, the memory 570 may store pieces of first projection data, pieces of second projection data, a reconstructed tomography image, etc.

Furthermore, the memory 570 may include at least one storage medium among a flash memory-type memory, a hard disk-type memory, a multimedia card micro-type memory, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The user interface 580 may receive a user input. For example, the user interface 580 may receive an input for setting a plurality of energy bands over which X-rays are detected.

In detail, the user interface 580 may receive a user input for setting a maximum value and a minimum value for each of the set plurality of energy bands according to a tube voltage. The user interface 580 may receive an input for setting the number of energy bands. Furthermore, the photon counting detector 560 may detect X-rays separately for each of the set plurality of energy bands.

The display 590 may display results obtained by scanning the object, such as a user interface screen and a tomography image.

Furthermore, the user interface 580 may be formed as a touch pad. In detail, the user interface 580 includes a touch pad combined with a display panel in the display 590 and outputs a user interface screen to the display panel. When a predetermined command is input via the user interface screen, the touch pad may detect the input of the predetermined command to recognize the predetermined command input by the user.

In detail, if the user interface 580 is formed as a touch pad, when the user touches a predetermined point on the user interface screen, the user interface 580 detects a touched point. The user interface 580 may then transmit information about the detected touched point to the image preprocessor 520 or the image reconstructor 530. The image preprocessor 520 or the image reconstructor 530 may then recognize a user request or command corresponding to a menu item displayed at the detected point and preprocess or reconstruct a tomography image according to the recognized user request or command.

Figure 6:
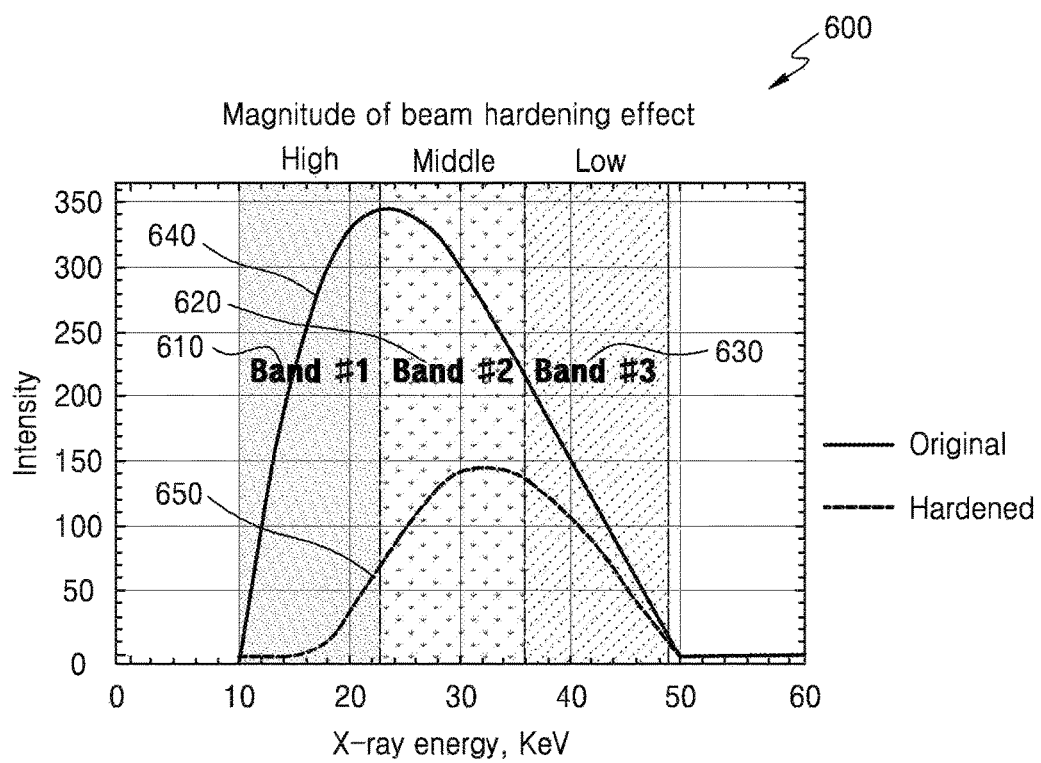
FIG. 6 is a graph of energy spectra of X-rays obtained before and after undergoing a beam hardening effect according to an exemplary embodiment.

FIG. 6 is a graph of energy spectra 600 of X-rays obtained before and after undergoing a beam hardening effect according to an exemplary embodiment.

In detail, FIG. 6 illustrates an energy spectrum 640 ("original") of X-rays generated by the X-ray generator 550 and an energy spectrum 650 ("hardened") of X-rays detected by the photon counting detector 560 after passing through an object. In other words, the graphs of energy spectra 640 and 650 respectively show X-ray energy spectra obtained before and after the X-rays undergo beam hardening effect.

For example, referring to FIG. 6, when a tube voltage is set to 50 kilovolt peak (kVp), the X-rays generated by the X-ray generator 550 may show a continuous distribution of energies up to 50 kiloelectorn volt (keV).

.As described above, the magnitude of a beam hardening effect may vary according to energy bands of photons. In detail, as energy bands become lower, an attenuation coefficient of the object may increase, and magnitude of a beam hardening effect may increase.

For example, if energy bands of X-rays are divided into a first band 610 of 10 keV to 22 keV, a second band 620 of 22 keV to 36 keV, and a third band 630 of 36 keV to 50 keV, the magnitude of a beam hardening effect may decrease in an order from the first band 610 to the third band 630.

Figure 7:
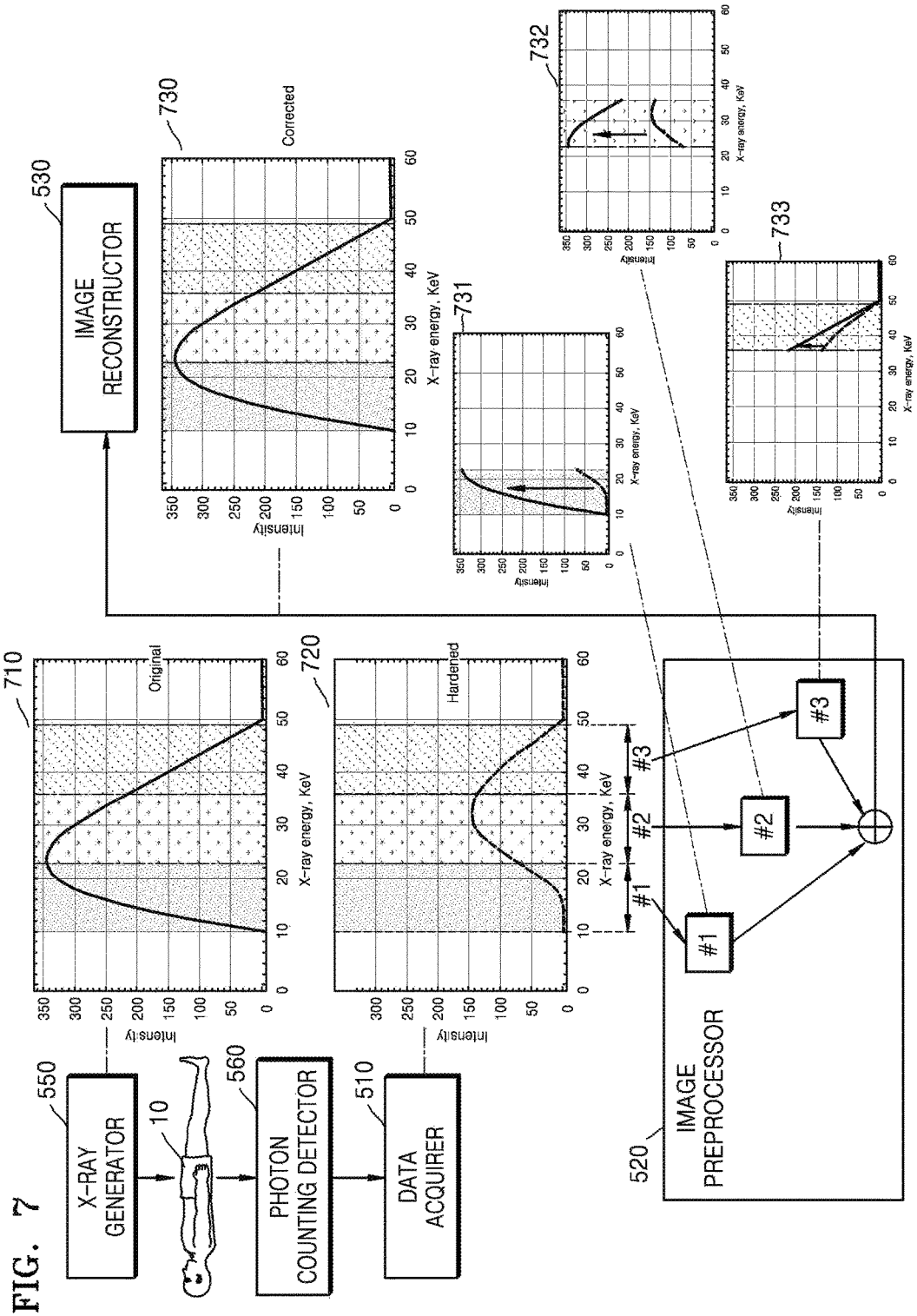
FIG. 7 is a conceptual diagram for explaining an operation of reconstructing a tomography image by correcting beam hardening, which is performed by a tomography imaging apparatus, according to an exemplary embodiment.

FIG. 7 is a conceptual diagram for explaining an operation of reconstructing a tomography image by correcting beam hardening, which is performed by the tomography imaging apparatus 500 of FIG. 5, according to an exemplary embodiment.

For example, if a tube voltage is 50 kVp, the X-ray generator 550 may generate X-rays having a continuous energy spectrum not exceeding 50 keV. The X-ray generator 550 may also emit the X-rays generated according to imaging conditions including a tube voltage toward the object 10.

Referring to FIG. 7, X-rays initially generated by the X-ray generator 550 may have a continuous energy spectrum 710.

The photon counting detector 560 may detect the X-rays that have passed through the object 10 separately for each of a plurality of energy bands. In detail, the photon counting detector 560 divides an energy spectrum having a maximum energy determined by a tube voltage into a plurality of energy bands and detects X-rays for each of the plurality of energy bands.

For example, the photon counting detector 560 may divide an energy spectrum into a first band of 10 keV to 22 keV, a second band of 22 keV to 36 keV, and a third band of 36 keV to 50 keV and detect X-rays for each of the first through third bands.

The data acquirer 510 may acquire pieces of first projection data of the object for each of the plurality of energy bands from the photon counting detector 560. Alternatively, the data acquirer 510 may acquire pieces of first projection data as the pieces of first projection data pass through the photon counting detector 560, a DAS, and a data transmitter.

Referring to FIG. 7, the first projection data acquired by the data acquirer 510 may have an energy spectrum 720. For example, the data acquirer 510 may acquire the pieces of first projection data of the object for each of a first band of 10 keV to 22 keV, a second band of 22 keV to 36 keV, and a third band of 36 keV to 50 keV into which the energy spectrum 720 is divided. As shown in the energy spectrum 720 of the first projection data, the magnitude of a beam hardening effect may increase gradually in the order from the third band to the first band.

In this case, the energy spectrum 720 of the first projection data acquired by the data acquirer 510 may be the same as the energy spectrum of the X-rays detected by the photon counting detector 560.

The image preprocessor 520 acquires pieces of second projection data for the object by performing a beam hardening correction process on pieces of first projection data for each of the plurality of energy bands.

For example, the image preprocessor 520 may perform a beam hardening correction process based on predetermined beam hardening correction coefficients corresponding to each of the plurality of energy bands. In other words, the image preprocessor 520 may correct beam hardening effects in pieces of first projection data, based on beam hardening correction coefficients set differently according to each of the plurality of energy bands.

In this case, a beam hardening correction coefficient may be a coefficient that is used in a predetermined arithmetic operation to remove artifacts caused by a beam hardening effect.

In detail, the image preprocessor 520 may perform a beam hardening correction process such as polynomial fitting or curve fitting according to Equation (1) below:

$$P_{C1} = a_{10} + a_{11} \cdot P_1 + a_{12} \cdot P_1^2 + a_{13} \cdot P_1^3 \ldots a_{1m} \cdot P_1^m$$

$$P_{C2} = a_{20} + a_{21} \cdot P_2 + a_{22} \cdot P_2^2 + a_{23} \cdot P_2^3 \ldots a_{2m} \cdot P_2^m$$

$$P_{C3} = a_{30} + a_{31} \cdot P_3 + a_{32} \cdot P_3^2 + a_{33} \cdot P_3^3 \ldots a_{3m} \cdot P_3^m$$

$$P_{Cn} = a_{n0} + a_{n1} \cdot P_n + a_{n2} \cdot P_n^2 + a_{n3} \cdot P_n^3 \ldots a_{nm} \cdot P_n^m \quad (1)$$

In this case, $P_1$ through $P_n$ respectively denote input values for the beam hardening correction process, i.e., pieces of first projection data corresponding to respective first through n-th energy bands, and $P_{c1}$ through $P_{cn}$ respectively denote output values for the beam hardening correction process, i.e., pieces of second projection data corresponding to respective first through n-th energy bands. $a_{10}$ through $a_{1m}$ denote beam hardening correction coefficients set for the first energy band, and $a_{n0}$ through $a_{nm}$ denote beam hardening correction coefficients for the n-th energy band.

As an order m of the beam hardening correction process increases, the image preprocessor 520 may perform the beam hardening correction process more precisely. For example, the image preprocessor 520 may perform a beam hardening correction process on pieces of first projection data via third-order polynomial fitting.

Furthermore, because the magnitude of a beam hardening effect increases as an energy band decreases, if the first energy band is the lowest energy band, the magnitude of correction between an output value $P_{c1}$ and an input value $P_1$ may be greater than the magnitude of correction between an output value $P_{c2}$ and an input value $P_2$.

Furthermore, the image preprocessor 520 may set beam hardening correction coefficients based on at least one among energy band, a tube voltage, and the number of slices to which the beam hardening correction coefficients correspond.

As described above, because the magnitude of beam hardening effect varies with energy band, beam hardening correction coefficients may have different values according to energy band to which the beam hardening correction coefficients correspond.

An energy spectrum of X-rays generated by the X-ray generator 550 may have different characteristics according to a tube voltage. Thus, values of beam hardening correction coefficients may vary according to the tube voltage. For example, a probability density function of an X-ray energy spectrum may take on different shapes depending on a tube voltage.

Characteristics of X-rays that have passed through the object 10 may vary according to the number of slices (or a slice thickness). Thus, a beam hardening correction coefficient may have a different value depending on the number of slices.

The image preprocessor 520 may set a beam hardening correction coefficient based on imaging conditions for a tomography image, other than energy band, a tube voltage, and the number of slices.

Furthermore, the image preprocessor 520 may acquire beam hardening correction coefficients corresponding to each of the plurality of energy bands by using a phantom.

For example, the tomography imaging apparatus 400 or 500 according to the exemplary embodiments may use a water phantom, an acryl phantom, a plastic phantom, or any other single-material phantom to obtain beam hardening correction coefficients for each of the plurality of energy bands.

The water phantom may be a representative phantom used to acquire beam hardening correction coefficients. Because about 70% to 80% of a human body is made of water, the tendency and characteristics of a beam hardening effect that occurs in a water phantom is similar to those of a beam hardening effect that occurs in a human body. Thus, by applying a beam hardening correction coefficient acquired using a water phantom to a tomography image of the human body, beam hardening artifacts that are introduced in the tomography image of the human body may be effectively removed.

The tomography image apparatus 400 or 500 may acquire a beam hardening correction coefficient by using a phantom having a similar composition to the human body, which is a mixture of various materials, other than a single-material phantom.

An operation of obtaining a beam hardening correction coefficient by using a water phantom, which is performed by the tomography imaging apparatus 400 or 500, will now be described in more detail with reference to FIGS. 8A and 8B. Furthermore, for convenience of explanation, it is assumed hereinafter that the tomography imaging apparatus 400 or 500 is included in the CT system 100 of FIGS. 1 and 2.

Figure 8A:
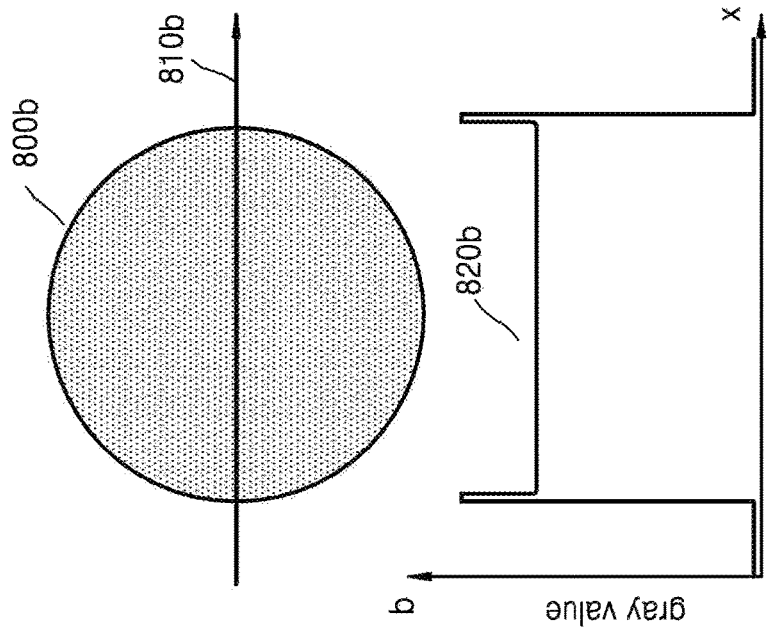
FIGS. 8A and 8B are respectively a tomography image and a graph of a water phantom that underwent beam hardening and a tomography image and a graph of a water phantom obtained after undergoing beam hardening correction, according to an exemplary embodiment.
Figure 8B:
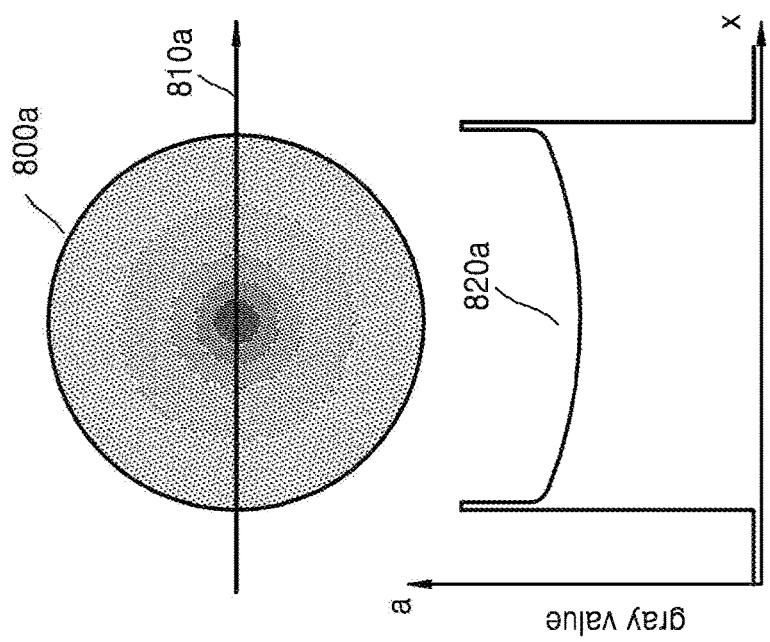

FIGS. 8A and 8B are respectively a tomography image and a graph of a water phantom that underwent beam hardening and a tomography image and a graph of a water phantom that has undergone beam hardening correction, according to an exemplary embodiment. In detail, FIG. 8A shows a CT image 800a of a water phantom that underwent beam hardening and a CT number 820a (a gray value a) along a predetermined axis 810a (e.g., an x-axis) passing through a center of the CT image 800a. FIG. 8B illustrates a CT image 800b of a water phantom after undergoing beam hardening correction and a CT number 820b (a gray value b) along a predetermined axis 810b (e.g., an x-axis) passing through a center of the CT image 800b.

Referring to FIG. 8A, due to a beam hardening effect, the CT number 820a decreases towards the center of the CT image 800a of the water phantom. Thus, the beam hardening effect may cause the CT image 800a to appear darker gradually toward the center of the water phantom.

On the other hand, referring to FIG. 8B, the CT number 820 in the CT image 800b of the water phantom that has undergone beam hardening correction has a constant value (e.g., 0). Thus, the CT image 800b that has undergone beam hardening correction may have uniform brightness. In other words, if a CT number in a CT image of the water phantom is constant, artifacts caused by a beam hardening effect may be removed.

The tomography imaging apparatus 400 or 500 according to an exemplary embodiment may set a plurality of beam hardening correction coefficients for each of a plurality of energy bands so that a CT number in a CT image of a water phantom remains constant via a beam hardening correction process.

In detail, the data acquirer 410 or 510 may acquire pieces of first projection data for a water phantom that are input values in Equation (1), and the image preprocessor 420 or 520 may set pieces of second projection data that are output values in Equation (1) so that a CT number in a CT image of the water phantom has a constant value. The image preprocessor 420 or 520 may also set beam hardening correction coefficients for each of a plurality of energy bands, based on the acquired pieces of first projection data of the water phantom, the set pieces of second projection data of the water phantom, and Equation (1).

Referring back to FIG. 7, for example, the image preprocessor 520 may perform a beam hardening correction process on the pieces of first projection data of the object 10 based on beam hardening correction coefficients acquired using a phantom, i.e., beam hardening coefficients $a_{10}$ through $a_{1m}$ for the first band of 10 keV to 22 keV, $a_{20}$ through $a_{2m}$ for the second band of 22 keV to 36 keV, and $a_{30}$ through $a_{3m}$ for the third band of 36 keV to 50 keV.

As shown in FIG. 7, the pieces of second projection data for the first through third bands may have energy spectra 731 through 733, respectively, and the total pieces of second projection data may have an energy spectrum 730.

Furthermore, the image reconstructor 530 may reconstruct a tomography image of the object 10 based on the pieces of second projection data.

Figure 9:
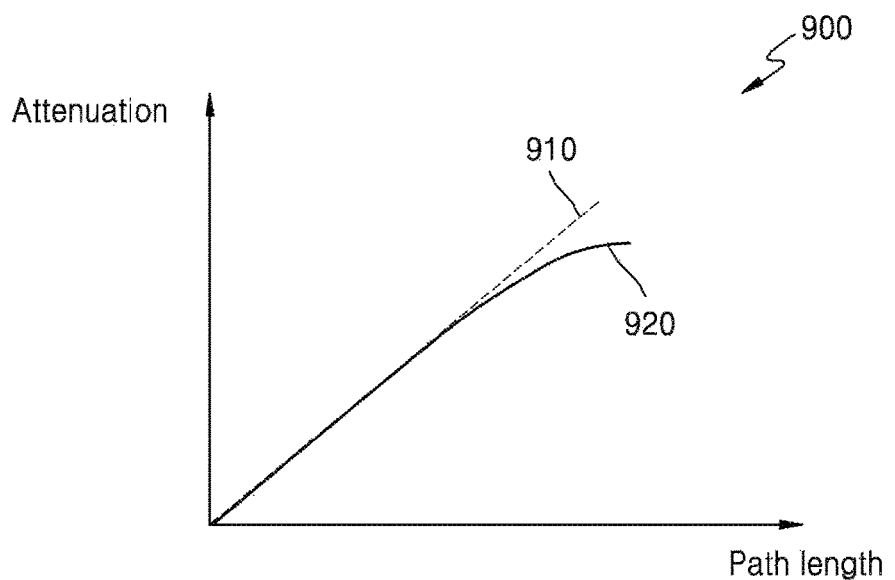
FIG. 9 is a graph of an attenuation degree with respect to a depth of penetration of an X-ray that underwent beam hardening according to an exemplary embodiment.

FIG. 9 schematically is graph of an attenuation degree 900 with respect to a depth of penetration of an X-ray that underwent beam hardening according to an exemplary embodiment.

As described above, when a beam hardening effect occurs, photons in a lower energy band are attenuated more readily than photons in a higher energy band. Thus, as a beam penetrates through an object, an average energy of the beam increases and penetrating power of the beam that passes through the object increases. As shown in FIG. 9, a slope (i.e., the attenuation degree 900) that is a rate of change in an attenuation amount 920 with respect to a depth of penetration (i.e., a path length) of a beam hardened X-ray may decrease as the depth of penetration increases.

On the other hand, if the beam hardening effect is corrected, because there is no change in average energy of a beam, penetrating power of the beam also remains unchanged even as a depth of penetration through an object increases. Thus, referring to FIG. 9, the slope (e.g., an attenuation degree) that is a rate of change in an attenuation amount 910 with respect to a depth of penetration of X-rays that have undergone beam hardening correction may remain constant regardless of the depth of penetration thereof.

Thus, the image preprocessor 420 or 520 may set beam hardening correction coefficients so that a slope that is a rate of change in an attenuation amount of X-rays with respect to a penetration depth remains constant along the penetration depth.

Figure 10:
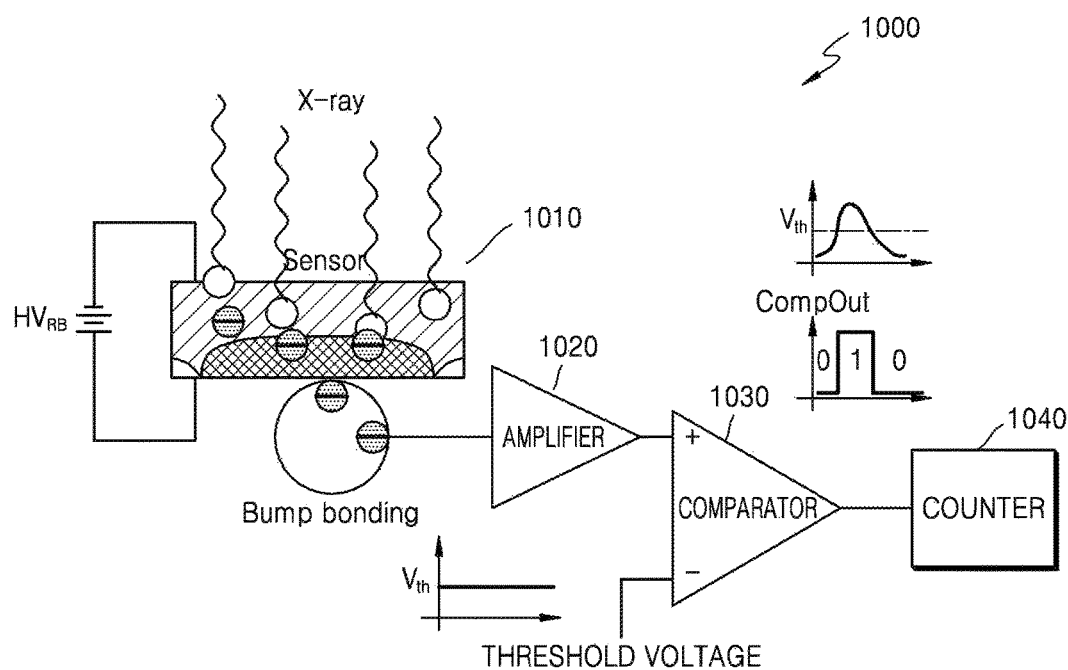
FIG. 10 is a diagram for explaining an operation of detecting X-rays by distinguishing between energies of the X-rays, which is performed by a photon counting detector, according to an exemplary embodiment.

FIG. 10 is a diagram for explaining an operation of detecting X-rays by distinguishing between energies of the X-rays, which is performed by a photon counting detector 1000, according to an exemplary embodiment.

The photon counting detector 1000 includes an X-ray sensor 1010, an amplifier 1020, at least one comparator 1030 for distinguishing between energies of detected X-rays, and a counter 1040.

In detail, the X-ray sensor 1010 and a DAS may be connected to each other by bump-bonding. Electron-hole pairs generated by X-rays may be transmitted to the amplifier 1020 of the DAS that in turn outputs a voltage signal corresponding to the electron-hole pairs. Then, the comparator 1030 may compare the voltage signal output from the amplifier 1020 with a externally controllable threshold voltage $V_{th}$, and output a value "1" if the voltage signal is greater than the threshold voltage and a value "0" if the voltage signal is less than the threshold voltage.

The counter 1040 may count values output from the comparator 1030. In detail, the counter 1040 may count the number of photons in emitted X-rays, which generate a voltage that is greater than or equal to the threshold voltage, by counting values "1" output from the comparator 1030.

Furthermore, the controller 540 of the tomography imaging apparatus 500 according to an exemplary embodiment may control a threshold voltage being applied to the comparator 1030 of the photon counting detector 1000, according to an input for setting a plurality of energy bands received by the user interface 580.

Figure 11:
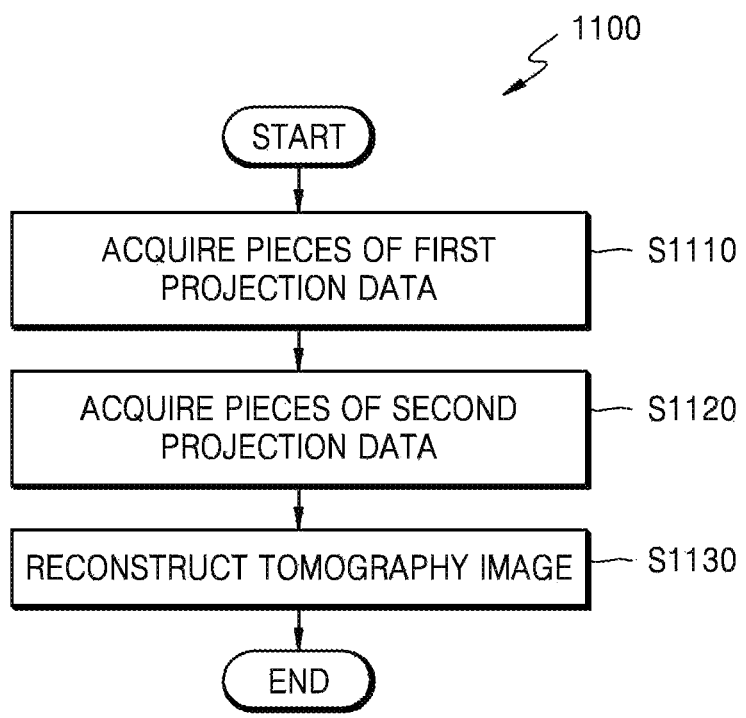
FIG. 11 is a flowchart of a tomography imaging method according to an exemplary embodiment.

FIG. 11 is a flowchart of a tomography imaging method 1100 according to an exemplary embodiment. The tomography imaging method 1100 may be performed by the tomography imaging apparatuses 400 and 500 described with reference to FIGS. 1 through 10. Operations of the tomography imaging method 1100 may have the same technical idea as corresponding operations performed by the components of the tomography imaging apparatuses 400 and 500. Thus, the same descriptions as those provided above with respect to FIGS. 1 through 10 are omitted.

Referring to FIG. 11, in the tomography imaging method 1100 according to an exemplary embodiment, pieces of first projection data of an object are acquired for each of a plurality of energy bands, from the photon counting detector (e.g., 560 of FIG. 5) for detecting X-rays separately for each of the plurality of energy bands (S1110). Furthermore, operation S1110 may be performed by the data acquirer 410 or 510 of the tomography imaging apparatus 400 or 500.

Furthermore, according to the tomography imaging method 1100, the photon counting detector (e.g., 560) may receive an input for setting the plurality of energy bands over which X-rays are detected.

In the tomography imaging method, 1100, pieces of second projection data of the object are acquired by performing a beam hardening correction process on the pieces of first projection data for each of the plurality of energy bands (S1120). Operation S1120 may be performed by the image preprocessor 420 or 520 of the tomography imaging apparatus 400 or 500.

In detail, the beam hardening correction process may be performed based on predetermined beam hardening correction coefficients corresponding to each of the plurality of energy bands.

In the tomography imaging method 1100, a tomography image of the object is reconstructed based on the pieces of second projection data (S1130). Operation S1130 may be performed by the image reconstructor 430 or 530 of the tomography imaging apparatus 400 or 500.

FIG. 12 is a flowchart of a tomography imaging method 1200 according to another exemplary embodiment.

Referring to FIG. 12, in the tomography imaging method 1200 according to another exemplary embodiment, beam hardening correction coefficients corresponding to each of a plurality of energy bands are acquired using a phantom (S1210). Operation S1210 may be performed by the image preprocessor 420 or 520 of the tomography imaging apparatus 400 or 500.

In detail, according to the tomography imaging method 1200, beam hardening correction coefficients may be set using a single-material phantom such as a water phantom, an acryl phantom, or a plastic phantom.

In the tomography imaging method 1200, X-rays are emitted toward an object (S1220). Operation S1220 may be performed by the X-ray generator 550 of the tomography imaging apparatus 500. In detail, the X-rays having a continuous energy spectrum may be generated according to a tube voltage and emitted toward the object.

In the tomography imaging method 1200, the X-rays are detected separately for each of the plurality of energy bands (S1230). Operation S1230 may be performed by the photon counting detector 560 of the tomography imaging apparatus 500.

According to the tomography imaging method 1200, an input for setting the plurality of energy bands over which X-rays are detected via the photon counting detector 560. Furthermore, a threshold voltage being applied to a comparator included in the photon counting detector 560 may be set according to the received input.

In the tomography imaging method 1200, pieces of first projection data for the object are acquired for each of the plurality of energy bands, from the photon counting detector 560 (S1240). Because operation S1240 may correspond to operation S1110, the same descriptions as those provided above with respect to FIG. 11 are omitted.

In the tomography imaging method 1200, pieces of second projection data of the object are acquired by performing a beam hardening correction process on the pieces of first projection data for each of the plurality of energy bands (S1250). Because operation S1250 may correspond to operation S1120, the same descriptions as those provided above with respect to FIG. 11 are omitted.

According to the tomography imaging method 1200, a tomography image of the object are reconstructed based on the pieces of second projection data (S1260). Operation S1260 may be performed by the image reconstructor 430 or 530 of the tomography imaging apparatus 400 or 500.

As described above, in the tomography imaging apparatus 400 or 500 and the tomography imaging method 1100 or 1200 according to the exemplary embodiments, a beam hardening effect may be corrected separately for each of the plurality of energy bands. Thus, artifacts caused by beam hardening may be effectively removed, and a tomography image having improved resolution may be provided.

In addition, the exemplary embodiments may also be implemented through computer-readable code and/or instructions on a medium, e.g., a computer-readable medium, to control at least one processing element to implement any above-described embodiments. The medium may correspond to any medium or media that may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A tomography imaging apparatus comprising:
a data acquirer configured to acquire first X-ray data of an object, for each of a plurality of energy bands;
an image preprocessor configured to:
set a plurality of beam hardening correction coefficients corresponding to each of the plurality of energy bands, the plurality of beam hardening correction coefficients comprising first beam hardening correction coefficients corresponding to a lowest energy band among the plurality of energy bands and second beam hardening correction coefficients corresponding to a highest energy band among the plurality of energy bands, and the first beam hardening correction coefficients being set to be greater in value than the second beam hardening correction coefficients; and
perform a beam hardening correction on the first X-ray data that is acquired, for each of the plurality of energy bands, based on the plurality of beam hardening correction coefficients that is set, to generate second X-ray data of the object; and
an image reconstructor configured to reconstruct a tomography image of the object, based on the second X-ray data that is generated.

2. The apparatus of claim 1, wherein the image preprocessor is further configured to set the plurality of beam hardening correction coefficients corresponding to each of the plurality of energy bands, based on either one or both of a tube voltage and a number of slices to which the plurality of beam hardening correction coefficients correspond.

3. The apparatus of claim 1, wherein the image preprocessor is further configured to determine the plurality of beam hardening correction coefficients corresponding to each of the plurality of energy bands, using a phantom.

4. The apparatus of claim 1, further comprising an interface configured to receive an input for setting the plurality of energy bands.

5. The apparatus of claim 1, further comprising an X-ray generator configured to emit X-rays toward the object.

6. The apparatus of claim 1, further comprising a photon counting detector configured to detect X-rays for each of the plurality of energy bands.

7. A tomography imaging method comprising:
acquiring first X-ray data of an object, for each of a plurality of energy bands;
setting a plurality of beam hardening correction coefficients corresponding to each of the plurality of energy bands, the plurality of beam hardening correction coefficients comprising first beam hardening correction coefficients corresponding to a lowest energy band among the plurality of energy bands and second beam hardening correction coefficients corresponding to a highest energy band among the plurality of energy bands, and the first beam hardening correction coefficients being set to be greater in value than the second beam hardening correction coefficients;
performing a beam hardening correction on the first X-ray data that is acquired, for each of the plurality of energy bands, based on the plurality of beam hardening correction coefficients that is set, to generate second X-ray data of the object; and
reconstructing a tomography image of the object, based on the second X-ray data that is generated.

8. The method of claim 7, wherein the setting the plurality of beam hardening correction coefficients comprises setting the plurality of beam hardening correction coefficients corresponding to each of the plurality of energy bands, based on either one or both of a tube voltage and a number of slices to which the plurality of beam hardening correction coefficients correspond.

9. The method of claim 7, further comprising determining the plurality of beam hardening correction coefficients corresponding to each of the plurality of energy bands, using a phantom.

10. The method of claim 7, wherein the setting the plurality of beam hardening correction coefficients comprises setting the plurality of beam hardening correction coefficients so that a gray value in the tomography image of a water phantom that is reconstructed remains constant after the beam hardening correction is performed.

11. The method of claim 7, wherein the setting the plurality of beam hardening correction coefficients comprises setting the plurality of beam hardening correction coefficients so that a rate of change in an attenuation amount of X-rays with respect to a penetration depth of the X-rays remains constant along the penetration depth.

12. The method of claim 7, further comprising receiving an input for setting the plurality of energy bands.

13. The method of claim 7, further comprising emitting X-rays toward the object.

14. The method of claim 7, further comprising detecting X-rays for each of the plurality of energy bands, using a photon counting detector.

15. A non-transitory computer-readable storage medium storing a program to cause a computer to perform the method of claim 7.

* * * * *